United States Patent [19]

Stokes

[11] Patent Number: 4,643,201
[45] Date of Patent: Feb. 17, 1987

[54] SINGLE-PASS A-V LEAD

[75] Inventor: Kenneth B. Stokes, Brooklyn Park, Minn.

[73] Assignee: Medtronic, Inc., Minneapolis, Minn.

[21] Appl. No.: 230,940

[22] Filed: Feb. 2, 1981

[51] Int. Cl.$^4$ .............................................. A61N 1/04
[52] U.S. Cl. ................................. 128/786; 128/419 P
[58] Field of Search ............. 128/419 P, 419 D, 784, 128/785, 786

[56] References Cited

U.S. PATENT DOCUMENTS

| 3,865,118 | 2/1975 | Bures | 128/419 P |
|---|---|---|---|
| 3,949,757 | 4/1976 | Sabel | 128/404 |
| 4,057,667 | 11/1977 | Lajos | 128/785 |
| 4,135,518 | 1/1979 | Dutcher | 128/419 P |
| 4,136,701 | 1/1979 | Barton et al. | 128/785 |
| 4,154,247 | 5/1979 | O'Neill | 128/419 P |

FOREIGN PATENT DOCUMENTS 2605590 8/1977 Fed. Rep. of Germany .
WO80/02801 12/1980 PCT Int'l Appl. .

Primary Examiner—William E. Kamm
Attorney, Agent, or Firm—Reed A. Duthler; Joseph F. Breimayer; John L. Rooney

[57] ABSTRACT

A single-pass body implantable lead for transvenous insertion through a single vein to simultaneously sense and/or stimulate the tissue of both the right atrium and right ventricle. The lead employs a single bifurcated connector at the proximal end. Insulated conductors for the ventricle and atrium are branched from a single outer sheath. The ventricular and atrial branches are established in fixed relation to one another. The ventricular branch is of sufficient length that it has excess length for the largest heart. The electrode of the ventricular branch is held within the right ventricular apex by tines. The atrial branch has a "J" shape imparted to the conductor coil. The atrial electrode is maintained in position within the right atrial appendage by tines. The ventricular branch is sufficiently flexible such that any excess length is merely coiled in some convenient position. The distal portion of the ventricular branch is made slightly more stiff than the proximal portion causing the excess length to loop within the atrium. Stylets are used to guide insertion.

4 Claims, 6 Drawing Figures

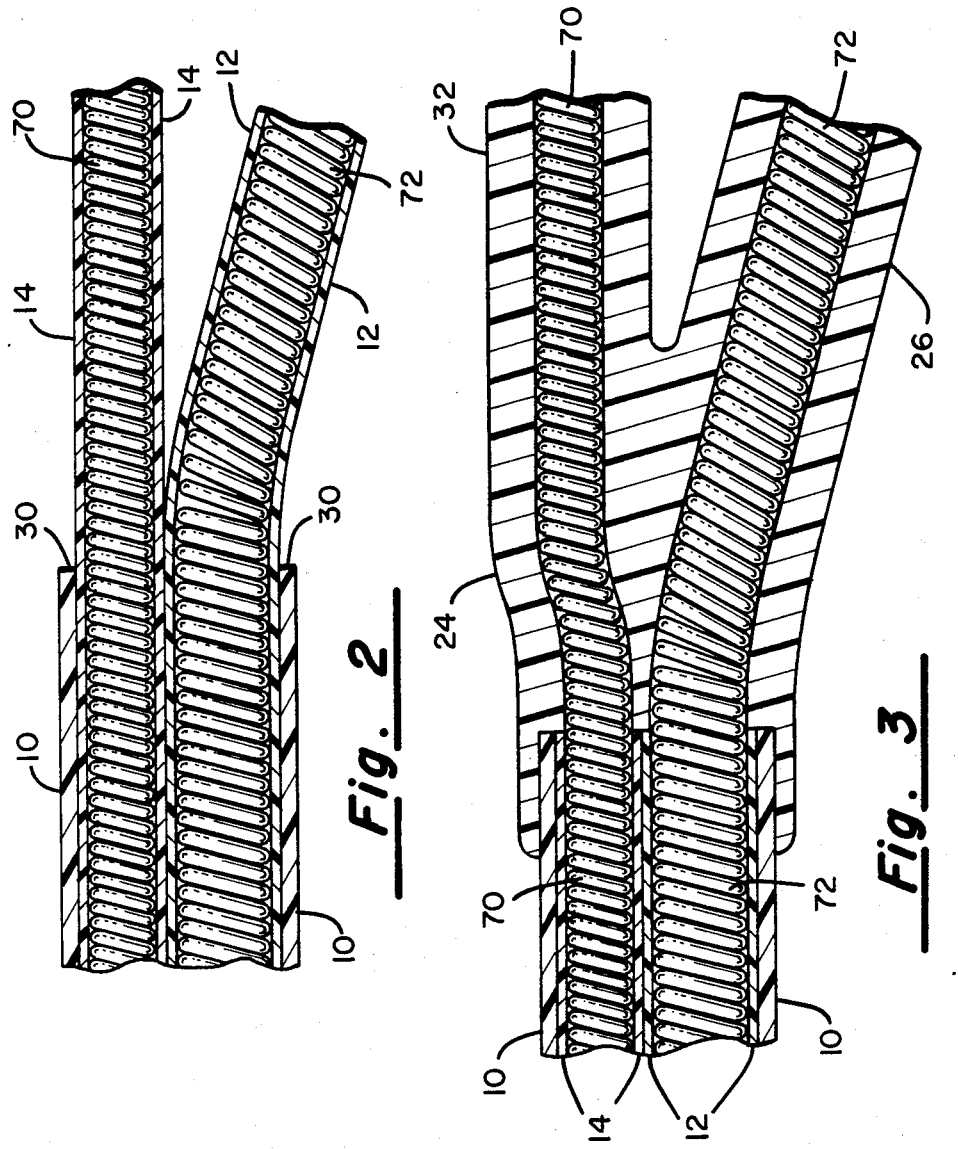

SINGLE-PASS A-V LEAD

BACKGROUND OF THE INVENTION

1. Field of the Invention

The present invention relates generally to body implantable leads, and more specifically relates to leads capable of interfacing with both the ventricle and atrium of the heart.

2. Description of the Prior Art

With the advent of atrial-ventricular (A-V) pacing, the necessity to electrically interface with both atrial and ventricular tissue has become a necessity. This may be accomplished through the use of two separate leads. One lead is placed in the atrium in the normal fashion whereas the second lead is placed within the ventricle in the normal fashion. Typical implant techniques use either a single vein for implantation of both leads or a separate vein for each of the leads to be introduced. A second approach and one thought to be simpler in implementation is the use of a single-pass lead.

U.S. Pat. No. 4,057,067 issued to Lajos is an example of a single-pass lead. The lead taught by Lajos has a single lead body which, at a point relatively near the distal end, results in a ventricular branch and an atrial branch. The ventricular and atrial branches are located at a fixed distance from one another. Therefore, the possible implant position of the ventricular electrode relative to the implant position of the atrial electrode is fixed and can not vary with variations in the size of the heart to be stimulated. The primary method for overcoming this problem is the use of single-pass leads employing the slider concept. The slider concept allows the length of the ventricular and atrial branches to be adjusted relative to one another. The slider concept is thus more easily implanted and makes provision for variations in heart size.

The major disadvantage of using the slider concept in a single-pass lead involves the difficulties associated with sealing the position at which the ventricular and atrial branches emerge from the common sheath. A second problem is experienced at the proximal end in connecting both branches to a common pulse generator. The assignee of the present invention has a number of patent applications on file which employ the slider conept in the single-pass A-V lead. These inventions tend to be directed toward a method of overcoming these difficulties associated with sealing the branchpoint and making proper connection to the common pulse generator.

The present invention does not employ the slider concept. Because the ventricular and atrial electrodes are at a fixed distance from one another, compensation must be made for variations in heart size. Leads which use something other than a straight line of transit between the electrode at the distal tip and the superior vena cava are also known. Dutcher, in U.S. Pat. No. 4,135,518 teaches a ventricular lead wherein the fixation technique involves use of some slack within the lead body. Dutcher uses a weighted distal tip in combination with a very flexible portion of the lead between the distal tip and some point proximal to that for encouraging enlodgement of the electrode in the right ventricular apex. It is interesting to note that Dutcher teaches the use of this slack within the lead to aid in fixation of the electrode and teaches only placement of this slack within the ventricle.

A second lead taught in U.S. Pat. No. 4,154,247 by O'Neill, uses a far more rigid amount of slack as a fixation means. O'Neill shows that a lead constructed in the manner in which he teaches can, through its rigidity, be forced to maintain contact with the tissue to be stimulated.

SUMMARY OF THE INVENTION

The present invention uses a single-pass lead which does not employ the slider concept. To compensate for variations in heart size the ventricular branch is longer than that required by the largest heart. The construction of the lead is such that the excess length of the ventricular branch is merely stored in the form of a coil within the atrium. To assist in placement of this excess the ventricular branch has a discontinuous flexibility. That is, the distal portion of the ventricular branch is slightly more stiff than the proximal portion. The coil thus formed is free to move about the atrium and has no effect upon the fixation. The position of the ventricular electrode within the right ventricular apex is maintained by tines located about the distal tip.

The atrial branch uses a memory coil which imparts to the atrial branch a "J" shape. This "J" shape enables the atrial electrode to be properly positioned within the atrial appendage. Tines about the atrial electrode also provide additional positional stability.

Proximal to the ventricular and atrial branches, a single outer sheath covers the lead. A single bifurcated connector is found at the proximal end. Stylets are used with each of the ventricular and atrial branches.

BRIEF DESCRIPTION OF THE DRAWINGS

FIG. 2 shows the point at which the ventricular and atrial branches separate.

FIG. 3 is a cross-sectional view of the bifurcation at the electrical connector found at the proximal end of the lead.

DETAILED DESCRIPTION OF THE PREFERRED EMBODIMENT

The preferred embodiment of the present invention is described in relation to a specific implementation of a single-pass A-V lead. Those of ordinary skill in the art will be able to readily apply the techniques taught herein to similar devices. The preferred embodiment is of a unipolar design for example. The modification of the lead taught herein to produce a bipolar style lead could be accomplished with that information readily available in the art.

Figure 1:
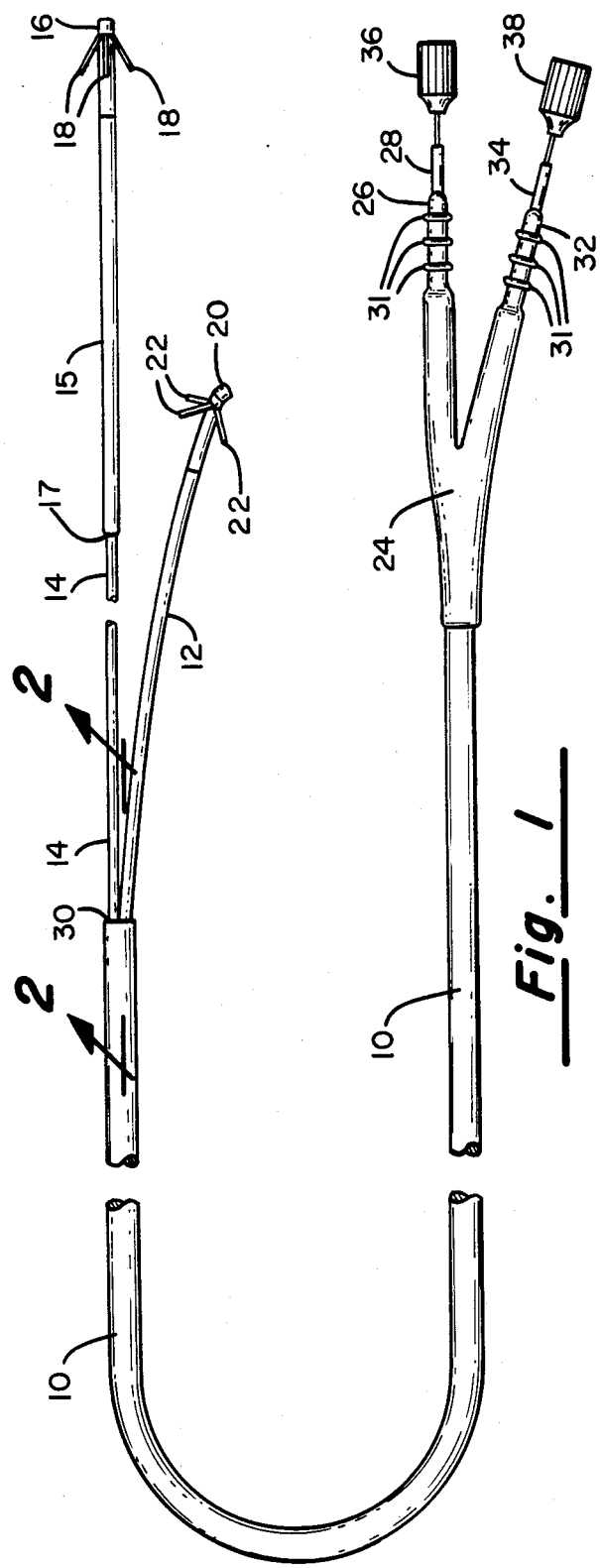
FIG. 1 is a plan view of a single-pass A-V lead employing the present invention.

FIG. 1 is a plan view of the single-pass A-V lead incorporating the present invention. Connector 24 is a standard bifurcated electrical connector attached to the proximal end of the lead. Connector pin 26 with corresponding metallic terminal pin 28 is connected to the atrial electrode. Similarly, connector pin 32 with metallic terminal pin 34 is coupled to the ventricular electrode. Stylet 36 is used to control the implantation of the atrial branch whereas stylet 38 is used to guide implantation of the ventricular branch. Sealing rings 31 are used to seal the connection with the pulse generator.

Outer sheath 10 is of a body compatible insulating material such as silicone rubber or urethane. It extends from bifurcated connector 24 to point 30 from which the ventricular and atrial branches emerge. The ventricular branch 14 is of relatively small cross-sectional diameter. It is of a material which permits maximum flexibility of the lead. Typical lead construction, in this case, would be the use of drawn-brazed-strand multifilar coil covered by an insulating sheath of urethane. Ventricular electrode 16 is located at the tip of the ventricular branch. Tines 18 are used for fixation of the ventricular electrode 16. From point 17 to electrode 16 the ventricular branch is covered by an additional sheath 15. The purpose of additional sheath 15 is to increase the stiffness of the portion of the ventricular branch between point 17 and the ventricular electrode 16. This distance is sufficiently small such that, with ventricular electrode 16 located at the right ventricular apex of the smallest heart to be implanted, point 17 is located within the right atrium. Notice that this produces a lead body with respect to the ventricular branch which is relatively stiff, proximal to point 30 and distal to point 17, and relatively flexible between points 30 and 17. The distance between point 30 and point 17, along the ventricular branch is sufficient that when the ventricular electrode is implanted, point 30 will be located proximal of the right atrium.

The atrial branch is made of a memory coil which assumes the familiar "J" shape upon removal of stylet 36. To fabricate a memory coil in this fashion, the cross-sectional area of the atrial branch is necessarily greater than the cross-sectional area of the ventricular, branch. The atrial branch is covered by outer sheath 12 of silicone rubber or urethane insulating material. Atrial electrode 20 is held in contact with the atrial wall by tines 22.

FIG. 2 is a cross-sectional view of the portion of the lead body wherein the ventricular and atrial branches separate. Notice that the ventricular branch consists of coil 70, covered by sheath 14. For simplicity the stylet 38 has been removed. Similarly, the atrial branch consists of coil 72 covered by insulating sheath 12. Proximal to point 30, the entire lead body is covered by outer sheath 10. Outer sheath 10 merely terminates at point 30, permitting the ventricular and atrial branches to separate. Care must be exercised to create a proper seal at point 30. This may be accomplished using medical adhesive or molding techniques.

FIG. 3 is a cutaway view of a portion of bifurcated connector 24. Notice that outer sheath 10 terminates within bifurcated cable 24, enabling proper sealing. Conductor coil 70 is conducted to connector pin 32 whereas conductor coil 72 from the atrial branch is conducted to connector pin 26. Notice also that sheath 14 from the ventricular branch and sheath 12 from the atrial branch extend the entire length of the lead to bifurcated connector 24. Care must be exercised to insure that an adequate seal is attained between sheath 10 and bifurcated connector 24. Additional seals created between bifurcated connector 24 and ventricular branch sheath 14 and between bifurcated connector 24 and atrial branch sheath 12 provide backup protection against the ingress of body fluids.

Figure 4:
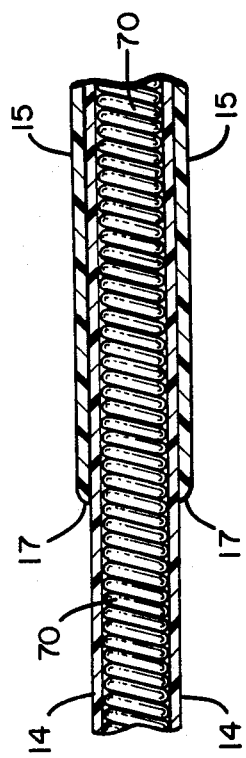
FIG. 4 shows a cross-sectional view of the point at which the flexibility of the ventricular branch is changed.

FIG. 4 is an enlarged cross-sectional view of the ventricular branch at point 17 wherein the ventricular branch is stiffened from point 17 to the distal tip. In the preferred embodiment this stiffening is accomplished by the use of additional sleeve 15 which is positioned between points 17 and the distal electrode. This sleeve is of an insulating material such as urethane or silicone rubber. This technique for increasing stiffness of the distal portion of the ventricular branch is preferred because of its simplicity. However, other methods may be used. For example, coil 70 may have increased stiffness distal to point 17. This may be accomplished by using a larger diameter wire or may be accomplished using stiffer materials. Sheath 14 could also be changed at point 17 to increase its thickness or to change its material to increase the stiffness. Each of these alternative techniques, although encompassed in the present invention as claimed herein, appear to be more costly than the preferred mode of using additional sleeve 15.

Figure 5:
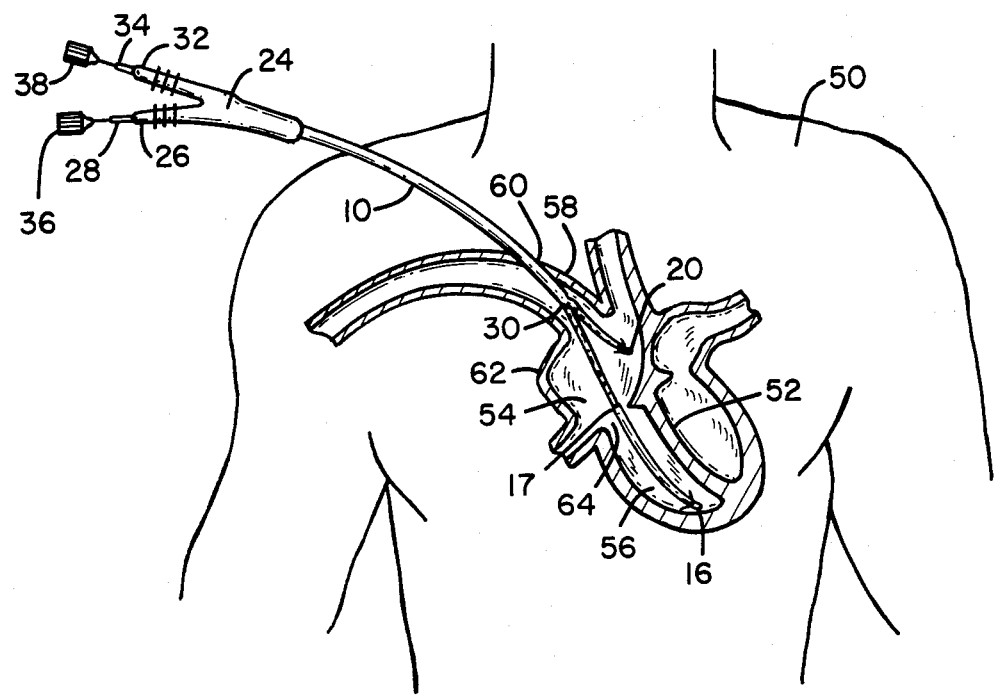
FIG. 5 is a schematic view of placement of the ventricular branch.

FIG. 5 is a schematic view of the present invention as used during implant. Stylets 36 and 38 are inserted into connector pins 26 and 32 respectively as shown. Ventricular electrode 16 is inserted into aperture 60 of vein 58 and guided into atrium 62, through valve 64, and into right ventricle 56. To be properly inserted the ventricular electrode 16 should be lodged within the right ventricular apex as shown. Stylet 38 is removed and sensing and stimulation thresholds are measured. Stylet 38 is reinserted and ventricular electrode 16 is repositioned as required.

Figure 6:
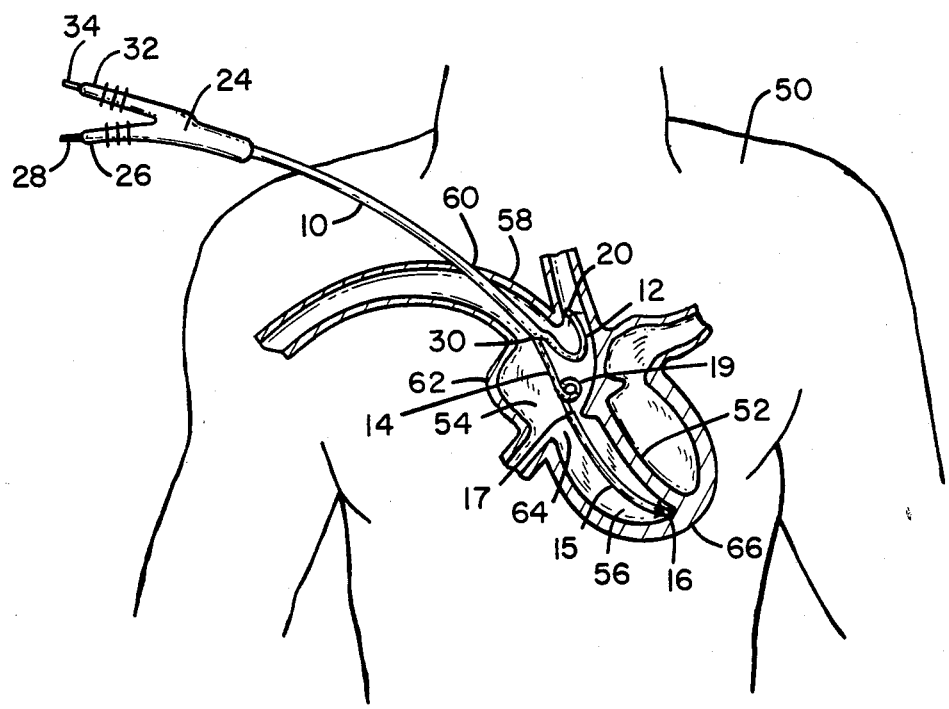
FIG. 6 is a schematic view of the single-pass lead after implantation of the atrial branch.

Following proper insertion of ventricular electrode 16, the position of the single-pass A-V lead is as shown in FIG. 5. Notice that the atrial branch is not located within the right atrium as the ventricular branch is sufficiently long that point 30 is within the superior vena cava. Stylet 38 is removed causing the ventricular branch to become extremely flexible. Using stylet 36, the atrial branch is advanced into right atrium 62. Reference to FIG. 6 shows that this advancement causes the excess length of the ventricular branch to form coil 19 within the atrium. The coil of excess length 19, should also fall within the atrium as the flexibility of the ventricular branch is greatest between points 30 and 17 as explained above. Notice that point 17 and point 30 are both within the right atrium. Removal of stylet 36 enables the atrial branch to assume its "J" shape upon relaxation. Notice this causes atrial electrode 20 to be located at the desired position within the right atrial appendage. Sensing and stimulation thresholds are measured and stylet 36 reinserted to reposition atrial electrode 20 as required. After the desired placement of the atrial electrode 20 has occurred, stylet 36 is removed and the implant is complete.

As explained above, the tendency for loop 19 of the excess length of the ventricular branch will be located within the right atrium. Should it be desired for any reason that this loop be located within the right ventricle. The desired result can be attained by inserting stylet 38 into connector pin 32 and (rolling) loop 19 through valve 64 into right ventricle 56. Connection to the pulse generator is accomplished in the normal manner known in the art.

Having thus described the preferred embodiment of the present invention, those of ordinary skill in the art will readily appreciate that the present invention may be readily applied to other leads having a variety of purposes somewhat different than discussed herein. It is also clear that these are within the scope of the present invention.

What is claimed is:

1. A single pass lead which may be implanted in a typical human heart, comprising:
   a connector;
   an atrial electrode for location in the right atrial appendage of said human heart when said lead is implanted in said human heart;
   a ventricular electrode for location in the right ventricular apex of said human heart when said lead is implanted in said human heart;
   an insulated atrial conductor having a proximal end coupled to said connector and a distal end coupled to said atrial electrode; and
   an insulated ventricular conductor substantially longer than said atrial conductor having a proximal end coupled to said connector and a distal end coupled to said ventricular electrode, said ventricular conductor fixedly attached to said atrial conductor from said connector to a first point a sufficient distance from said atrial electrode that when said atrial electrode is located in the right atrial appendage of said human heart, said first point is also located within the right atrium of said human heart, said ventricular conductor having sufficient length that when said ventricular conductor is fully extended and said ventricular electrode is located in the right ventricular apex of said human heart, said first point is located within the superior vena cava of said human heart, whereby when said lead is implanted in said human heart, said ventricular conductor is not fully extended and exhibits slack.

2. A single pass body implantable lead according to claim 1 wherein said ventricular conductor is comprised of a first segment having a first flexibility, running from said first point to a second point intermediate said first point and said ventricular electrode, and of a second segment having a second lesser flexibility, running from said second point to said ventricular electrode, whereby when said lead is implanted in said human heart, the slack exhibited by said ventricular conductor is located in said first segment.

3. A single-pass body implantable lead according to claim 1 wherein said second point is located proximal of said ventricular electrode such that when said ventricular electrode is located at the right ventricular apex of a large heart, said second point is located within the right atrium.

4. A single pass body implantable lead according to claim 3 wherein the slack exhibited by said ventricular conductor takes the form of a loop.

* * * * *